United States Patent [19]
Jorgenson

[11] Patent Number: 5,326,262
[45] Date of Patent: Jul. 5, 1994

[54] METHOD OF MAKING CUSPLESS ARTIFICIAL DENTITION

[76] Inventor: H. Grant Jorgenson, 9 Southampton Drive, SW., Calgary, Alberta, Canada, T2W 0T9

[21] Appl. No.: 983,693

[22] Filed: Dec. 1, 1992

[51] Int. Cl.⁵ .......................................... A61C 13/08
[52] U.S. Cl. ................................ 433/197; 433/196
[58] Field of Search ............................ 433/197, 196

[56] References Cited

U.S. PATENT DOCUMENTS

| | | | |
|---|---|---|---|
| Re. 23,607 | 12/1952 | Donavan | 433/197 |
| 1,878,517 | 9/1932 | Hiltebrandt | 433/197 |
| 1,963,207 | 6/1934 | Lothy | 433/197 |
| 1,987,712 | 1/1935 | Schroder et al. | 433/197 |
| 2,141,487 | 12/1938 | Pleasure | 433/197 |
| 2,416,983 | 3/1947 | Dickson | 433/197 |
| 2,417,965 | 3/1947 | Beresin | 433/197 |
| 3,316,639 | 5/1967 | Shovers | 433/197 |

FOREIGN PATENT DOCUMENTS

| | | | |
|---|---|---|---|
| 79816 | 12/1950 | Czechoslovakia. | |
| 544716 | 12/1930 | Fed. Rep. of Germany. | |
| 1150778 | 6/1963 | Fed. Rep. of Germany | 433/197 |
| 1230521 | 12/1966 | Fed. Rep. of Germany. | |
| 311691 | 7/1929 | United Kingdom | 433/197 |
| 782457 | 9/1957 | United Kingdom. | |

Primary Examiner—John J. Wilson
Attorney, Agent, or Firm—Jerry T. Kearns

[57] ABSTRACT

Artificial posterior cuspless teeth possess slightly convex functional occlusal surfaces in both mesiodistal and buccolingual directions on upper posterior teeth and slightly concave functional occlusal surfaces on lower posterior teeth, with both upper and lower posterior teeth configured to conform to the restored curves of Spee in an anterior—posterior direction and to conform to the restored curves of Wilson in a buccolingual direction.

2 Claims, 3 Drawing Sheets

(NATURAL DENTITION)

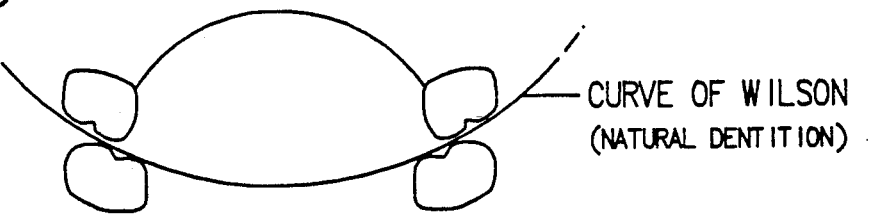
Fig. 3 — CURVE OF WILSON (NATURAL DENTITION)
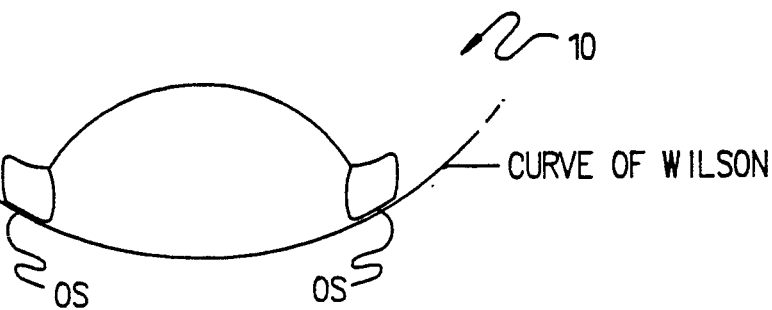
Fig. 4 — CURVE OF WILSON
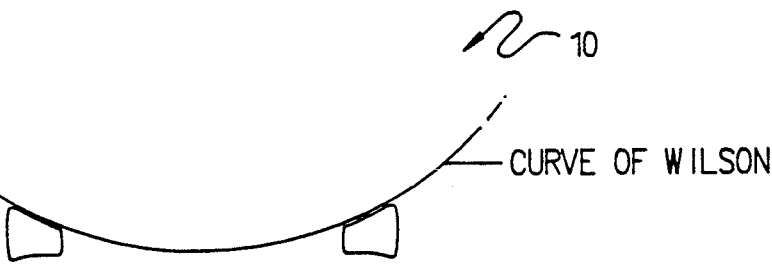
Fig. 5 — CURVE OF WILSON
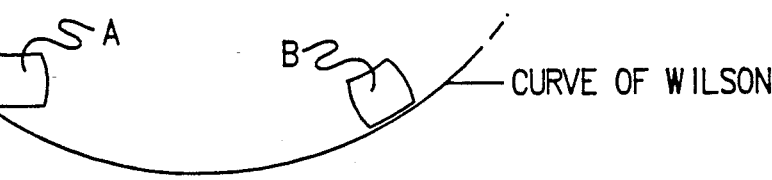
Fig. 6 — CURVE OF WILSON
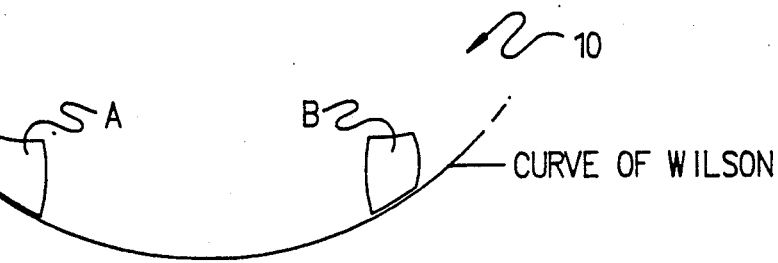
Fig. 7 — CURVE OF WILSON (NATURAL DENTITION)

(NATURAL DENTITION)

METHOD OF MAKING CUSPLESS ARTIFICIAL DENTITION

BACKGROUND OF THE INVENTION

1. Field of the Invention

The present invention relates to artificial teeth, and more particularly pertains to improved artificial posterior teeth for use in cases where the patient is completely edentulous (without teeth) and especially in cases where the edentulous ridges have been extensively resorbed or have shrunk away.

2. Description of the Prior Art

A variety of methods, some of them drastic and involving surgery and implants, have been developed to try to make dentures possessing greater stability and retention. Such surgical and implant methods expose the patient to risk and high costs.

The posterior teeth that are presently being used in dentures are generally cusped and designed to be set up in what is called a balanced occlusion. This means that a very accurate bite or centric occlusion must be established in the production of the denture. In all cases, if there is any error in setting up these teeth or even a minor amount of ridge resorption after the dentures are inserted, cusp interference will set up lateral forces which will tend to dislodge the denture when lateral or protrusive excursions are made.

The other most common type of posterior teeth presently used in dentures are those with flat occlusal surfaces known as zero degree teeth. These teeth are set up in a flat plane and as soon as the wearer of dentures moves into lateral or protrusive excursions there is no balancing occlusion. In other words, the wearer loses contact of many opposing posterior teeth and destabilizing forces are the probable outcome.

SUMMARY OF THE INVENTION

Accordingly, it is an object of the present invention to provide new and improved artificial teeth which can be used to develop dentures which possess greater stability than any dentures presently available. It is believed that ill fitting and unstable dentures cause more rapid resorption of the dental ridges. Thus, the provision of more stable dentures will help maintain the ridges and therefore keep the edentulous patient more dentally fit.

Additionally, dentures that are unstable and loosened during chewing are difficult for the wearer to use and cause a great many sore spots for the patient. A further object of the invention is to minimize such patient discomfort through the provision of more stable dentures.

Yet another object of the invention is the provision of improved artificial posterior teeth suitable for use in implants, resulting in the prevention of destabilizing forces and a concomitant reduction in stress on the implant.

An additional object of the invention is the provision of artificial posterior cuspless teeth designed especially to prevent any instability to the denture, and to give maximum balanced occlusal contact in centric occlusion and all excursions.

Yet another further object of the invention is to allow for greater error in the setting up of the teeth because a slight error in taking centric relation is less likely to cause great problems as in conventional techniques employing cusped teeth. Cusps on teeth interfere with centric occlusion and lateral excursions very quickly if they are not placed precisely where they should be. Because the technique of the invention is less sensitive, it is believed that dentures can be produced more easily and cheaply than prior art dentures. For the same reasons, a slight amount of resorption of the ridge will produce fewer problems as compared with prior art dentures. Dentures produced according to the present invention will be more comfortable for the patient to wear because they are designed to be stable and to stay in uniform contact throughout all excursions without any destabilizing forces. All forces applied from the lower denture to the upper denture will tend to keep each denture stabilized in place. Fewer sore spots after inserting the dentures will result in fewer dental appointments being necessary.

In order to achieve these and other objects of the invention, the present invention provides improved cuspless artificial teeth which include slightly convex functional occlusal surfaces in both mesiodistal and buccolingual directions on upper posterior teeth and slightly concave functional occlusal surfaces on lower posterior teeth, with both upper and lower posterior teeth configured to conform to the restored curves of Spee in an anterior—posterior direction and to conform to the restored curves of Wilson in a buccolingual direction.

These and various other advantages and features of novelty which characterize the invention are pointed out with particularity in the claims annexed hereto and forming a part hereof. However, for a better understanding of the invention, its advantages, and the objects obtained by its use, reference should be made to the drawings which form a further part hereof, and to the accompanying descriptive matter, in which there is illustrated and described preferred embodiments of the invention.

BRIEF DESCRIPTION OF THE DRAWINGS

FIG. 3 is a frontal sectional view through the molars of upper and lower models of natural dentition depicting an arc described touching the tips of the cusps in a bucco-lingual direction. This arc is known as the "curve of Wilson".

FIG. 4 is a frontal sectional view through the molars of an upper model of dentition showing the occlusal surface of the upper teeth of the present invention to be segments of the curve of Wilson.

FIG. 5 is a frontal sectional view through the molars of a lower model of dentition showing the occusal surface of the lower teeth of the present invention to be segments of the curve of Wilson.

FIG. 6 is a frontal sectional view through the molars of a dentition model which attempts to use a flat or zero degree tooth in the technique of the present invention.

FIG. 7 is a frontal sectional view through the molars of an upper model of dentition employing artificial teeth according to the present invention and illustrating the substantially vertical buccal teeth surfaces and the very slightly convex occusal teeth surfaces which follow the curve of Wilson.

DESCRIPTION OF THE PREFERRED EMBODIMENT(S)

Figure 1:
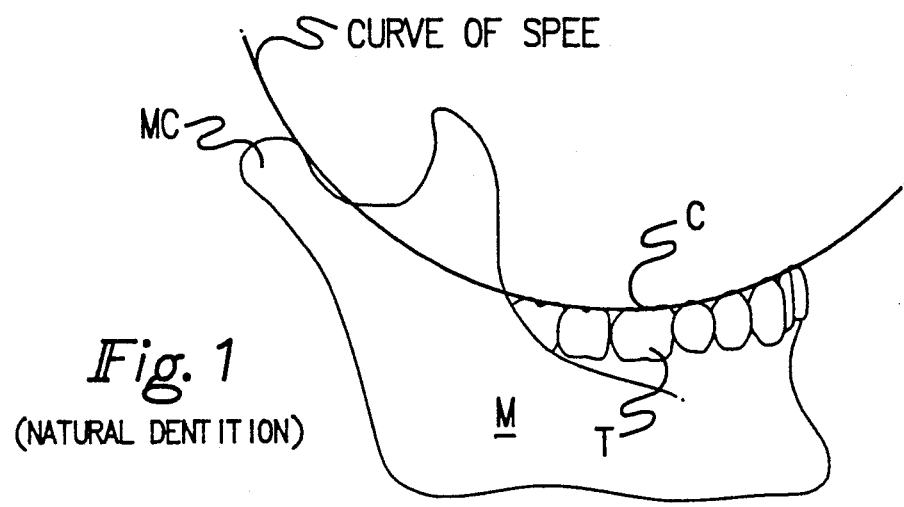
FIG. 1 is a side elevational view illustrating a mandible with natural teeth and depicting how a curve touching the tips of cusps of teeth tends to form an arc known as "the curve of Spee".

Referring now to the drawings, wherein like reference numerals designate corresponding structure throughout the views, and referring in particular to FIG. 1, it will be noted that natural teeth T in a lower mandible M possess cusps C, the tips of which lie on an arc known in the dental field as "the curve of Spee".

Figure 8:
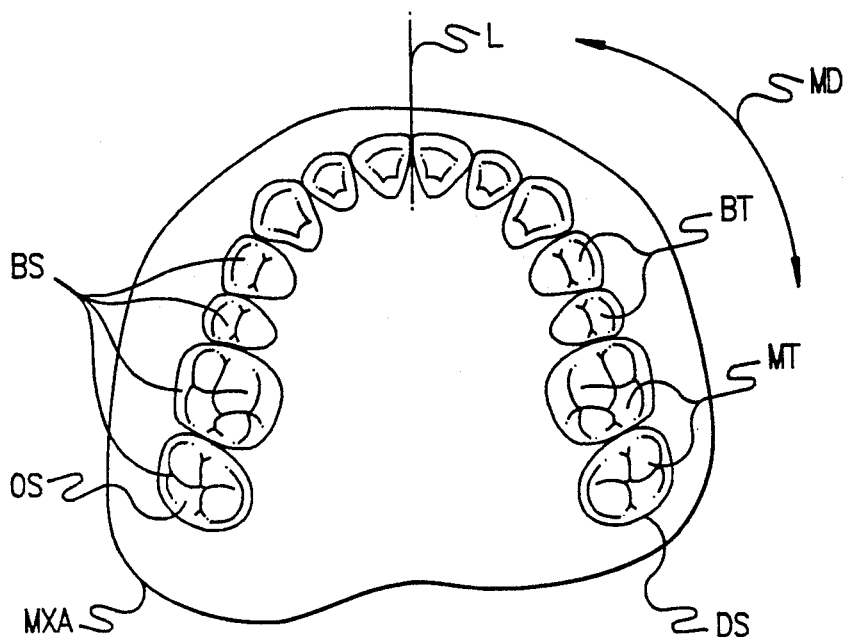
FIG. 8 is a plan view illustrating an upper model of natural dentition.
Figure 9:
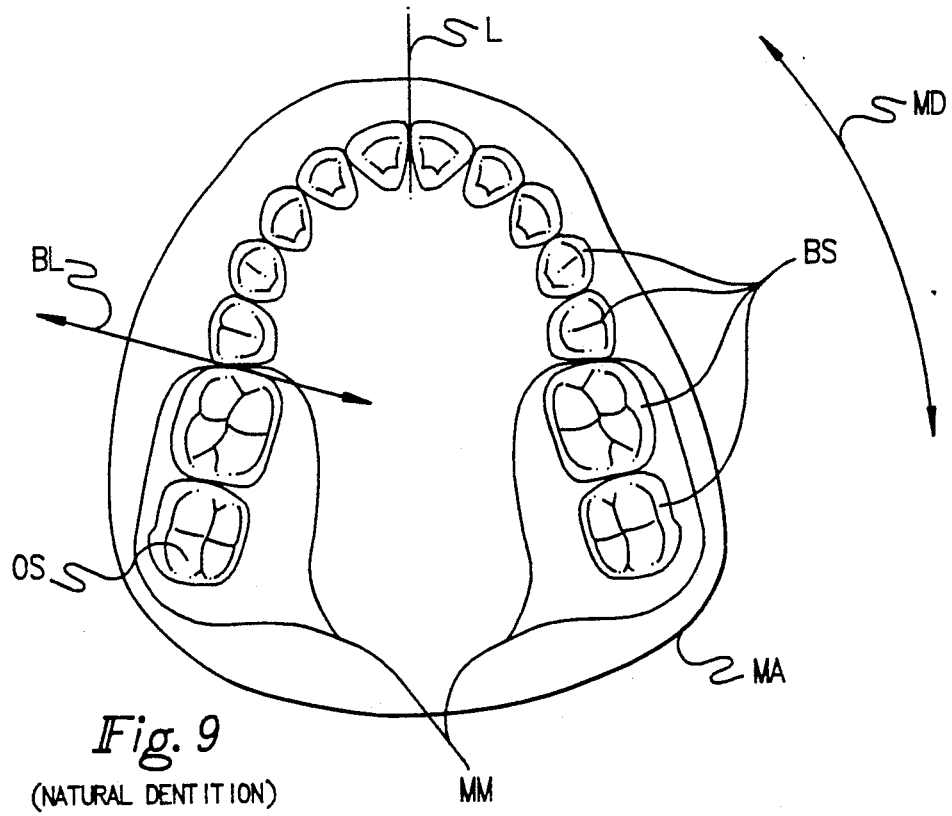
FIG. 9 is a plan view illustrating a lower model of natural dentition.

As can be appreciated from the plan views of upper and lower models of natural dentition illustrated respectively in FIGS. 8 and 9, the mesiodistal direction MD is defined by a line that follows the arch of the teeth from a median line L to the distal surface DS of the second molar. The occlusal surfaces OS of the teeth are the facing biting surfaces. The maxilla is the upper jaw, and the maxillary molars are the upper molars. The buccolingual direction BL (FIG. 9) is the direction from the cheek side of a tooth to the tongue side, and the buccal tooth surfaces BS are the side surfaces facing the cheek.

Figure 2:
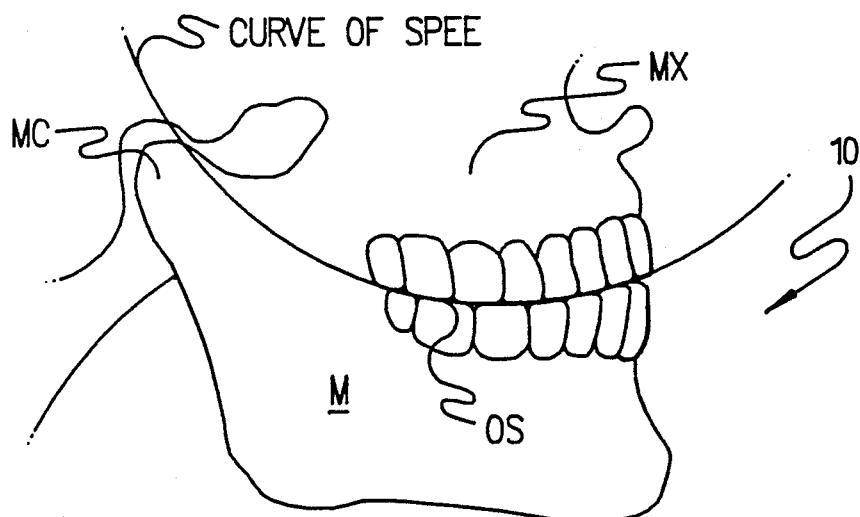
FIG. 2 is a side elevational view illustrating how the mandibular artificial teeth of the present invention possess occlusal surfaces of each tooth which form a segment of the curve of Spee.

As shown in FIG. 2, the artificial posterior teeth, both upper and lower, according to the present invention form segments of the curve of Spee in a mesiodistal direction on the occlusal surface. As a result, the teeth will slide freely in an anterior-posterior direction as the mandible M moves forward or backward and will remain in contact with opposing teeth on both sides of the arch. The curvature (curve of Spee) is such that the most posterior teeth may be moving down and forward, as the mandibular condyle MC does in a forward movement, while the more forward of the posterior teeth may actually be moving forward and upward and yet all teeth are still in full contact and all forces applied in an occlusal direction will be directed perpendicular to the curve of Spee.

FIG. 3 shows a frontal sectional view of natural dentition as well as a line called the "curve of Wilson". This curve is in a buccolingual direction and is such that the surfaces OS of the mandibular molars MM (FIG. 9) direct forces outwardly against the mandible M while those of the maxillary molars direct forces inwardly against the maxilla MX. This is true even though natural teeth have cusps on them. This invention proposes teeth which are segments of these arcs (curves of Wilson) on the occlusal surfaces OS, but without having cusps on them (FIGS. 4 and 5). This will allow teeth on the right side of the mandible to move to the right and upward in a lateral excursion to the right while the left side of the mandible M moves downward forward and to the right in that same excursion. At all times the upper and lower teeth will remain in full contact on both sides of the arch when occlusal pressure is applied and there is no food in the mouth. Pressure applied in an occlusal direction will then be applied perpendicular to the curves of Wilson in a buccolingual direction BL so that forces in the mandibular arch MA (FIG. 9) will be directed downward and outward and in the maxillary arch MXA (FIG. 8) those forces will be directed in an upward and inward direction. The mandibular arch MA (FIG. 9) is generally larger than the maxillary arch MXA (FIG. 8) in that the ridge of the mandible is generally outside the ridge of the maxilla, i.e. buccally to it. The forces applied to these teeth will therefore always tend to seat the denture in all directions. Excursions of the mandible M to the opposite side will react in a similar fashion.

What has been described is recognized as the simplest form of the occlusal surfaces OS of the teeth of this invention. In the simplest form, the occlusal surface OS of the upper molars MT and bicuspids BT (FIG. 8) would be slightly convex both mesiodistally MD and buccolingually BL. The slopes of the occlusal surfaces OS from buccal to lingual will be downward following the restored curves of Wilson.

Because of esthetics and even chewing efficiency it may be better to make adjustments and modifications to these occlusal surfaces to better serve the patients using them. It would be better to make the teeth appear as much like cusped teeth as possible for appearance and marginal ridges would add to the function of the teeth. Other indentations in the occlusal surfaces may help both appearance and function. Therefore, it is suggested that the occlusal surfaces of these teeth be modified as much as possible for appearance and efficiency as long as the principles outlined above are followed: i.e. forces will at all times be directed perpendicular to the restored curves of Spee and Wilson when occlusal forces are applied and there is nothing between the teeth. The upper and lower teeth will also be designed to slide freely anteriorly and posteriorly as well as in lateral excursions without any interference along the restored curves of Wilson and Spee.

For the sake of simplicity the occlusal surfaces of the teeth in this invention have been described as following the restored curves of Spee in a posterior anterior direction and of following the restored curves of Wilson in a buccolingual direction. However, because of the movements of the mandible and the slopes of the articular eminences it may turn out that the best occlusal curves for the teeth would be modified somewhat. For the sake of simplicity it should be assumed that when the terms "restored curves of Spee and Wilson" are used that a bit of modification may be implied because of mandibular movements and temporomandibular joints.

I have used zero degree teeth in trying to make dentures as outlined above, but theses teeth ideally should have a slightly convex surface on the uppers and a slightly concave surface on the lowers for my technique. It has also been found that the occlusal surface OS of a flat or zero degree tooth is horizontal in a buccolingual BL direction when the buccal surface BS of the tooth is in proper position for esthetics (FIG. 6 at A). In my technique, the occlusal surface OS of the tooth slopes downward from buccal to lingual BL following the curve of Wilson when the buccal surface BS is properly placed for esthetics. If the flat tooth occlusal surface OS is aligned with the curve of Wilson as close as possible, the slope of the buccal surface BS is inclined too far medially in an occlusal to gingival direction (FIG. 6 at B). FIG. 7 at A and B shows how these problems are corrected by the instant invention.

The curvatures in the arcs of the restored curves of Wilson and Spee will vary from patient to patient, depending upon the sizes of the maxillas and mandibles involved and also on their relationship to each other. The curves which allow maximum contact of the occlusal surfaces will also be affected by the shape and function of the temporomandibular joint. The present invention provides artificial teeth which restore the occlusion for all these natural curves to give maximum balanced occlusal contact in centric occlusion and all excursions.

The teeth according to the present invention may be made of porcelain, plastic, metal, or other materials.

It is to be understood, however, that even though numerous characteristics and advantages of the present invention have been set forth in the foregoing description, together with details of the structure and function of the invention, the disclosure is illustrative only, and changes may be made in detail, especially in matters of shape, size and arrangement of parts within the principles of the invention to the full extent indicated by the broad general meaning of the terms in which the appended claims are expressed.

What is claimed is:

1. A method of making cuspless artificial dentition comprising the steps of:
    forming upper posterior teeth with functional occlusal surfaces;
    forming lower posterior teeth with functional occlusal surfaces;
    configuring and disposing said upper and lower posterior teeth to conform to the restored curves of Spee in an anterior posterior direction and to conform to the restored curves of Wilson in a buccolingual direction.

2. The method of claim 1, further comprising the step of forming said occlusal surfaces on said upper teeth slightly convexly both mesiodistally and buccolingually.

UNITED STATES PATENT AND TRADEMARK OFFICE
CERTIFICATE OF CORRECTION

PATENT NO. : 5,326,262
DATED : July 5, 1994
INVENTOR(S) : R. Grant Jorgenson

It is certified that error appears in the above-indentified patent and that said Letters Patent is hereby corrected as shown below:

On the title page

The inventors address should read:

91 Southampton Drive S.W.,
Calgary, Alberta, Canada, T2W 0T9

Signed and Sealed this

Sixth Day of December, 1994

*Attest:*

BRUCE LEHMAN

*Attesting Officer*     *Commissioner of Patents and Trademarks*